United States Patent

Shimatani et al.

[11] Patent Number: 5,118,516
[45] Date of Patent: Jun. 2, 1992

[54] PRODUCTION PROCESS OF SIALICACIDS-CONTAINING LACTOSE

[75] Inventors: Masaharu Shimatani, Sayama; Yuzi Murakami, Tokorozawa; Tadashi Idota, Kawagoe; Kazuo Ido, Hino, all of Japan

[73] Assignee: Snow Brand Milk Products Company, Limited, Hokkaido, Japan

[21] Appl. No.: 489,570

[22] Filed: Mar. 7, 1990

[30] Foreign Application Priority Data

Mar. 10, 1989 [JP] Japan .................................. 1-58630

[51] Int. Cl.⁵ .................... A23C 9/144; A23C 9/146
[52] U.S. Cl. .................... 426/271; 426/239; 426/491; 426/580; 426/583
[58] Field of Search .............. 426/580, 583, 271, 495, 426/491, 239

[56] References Cited

U.S. PATENT DOCUMENTS

| | | | |
|---|---|---|---|
| 4,042,576 | 8/1977 | Eustache | 426/583 |
| 4,497,836 | 2/1985 | Marquardt et al. | 426/583 |
| 4,762,822 | 8/1988 | Ettinger | 426/335 |
| 4,844,923 | 7/1989 | Herrmann | 426/583 |
| 4,925,680 | 5/1990 | Schweikhardt et al. | 426/580 |

Primary Examiner—Jeanette Hunter
Assistant Examiner—Helen Pratt
Attorney, Agent, or Firm—Millen, White & Zelano

[57] ABSTRACT

Lactose containing physiologically-active sialic acids can be obtained by isolating and recovering the sialic acids together with lactose from a permeate or deproteinization solution obtained by ultrafiltration or heat treatment of whey or skim milk. The sialic acids-containing lactose is useful as an effective ingredient for foods, drugs, feeds, etc.

7 Claims, No Drawings

PRODUCTION PROCESS OF SIALICACIDS-CONTAINING LACTOSE

BACKGROUND OF THE INVENTION

1) Field of the Invention

This invention relates to a process for producing sialic acids-containing lactose from sialic acids containing milk-derived liquid such as whey or skim milk.

Owing to the inclusion of physiologically-active sialic acids, sialic acid-containing lactose are useful as an effective ingredient for foods, drugs, feeds, etc.

2) Description of the Prior Art

Lactose, sialic acids, ash, etc. are contained in addition to whey proteins or milk proteins in whey by-produced upon production of cheese or casein from milk as a starting material or in skim milk also by-produced upon separation and collection of milk fat from milk.

Among these components of whey or skim milk, whey proteins, milk proteins, lactose and the like have been isolated by ultrafiltration, heating, crystallization, or the like and have been used for respective applications.

Although sialic acids have been recognized to be physiologically effective for human bodies, sialic acids contained in whey or skim milk have scarcely been utilized because no low-cost industrial technique has yet been established for the isolation of sialic acids from a permeate obtained by ultrafiltration of whey or skim milk or a deproteinization solution obtained by heat treatment of whey or skim milk. Accordingly, they have heretofore been discarded along with such permeates or deproteinization solutions.

However, it has been reported recently that saccharide chains contained in a conjugated saccharide such as a glycoprotein or glycolipid play an important role for the intercellular recognition in the living body. It is now increasingly recognized that sialic acids are particularly important as essential constituents of a receptor which performs the intercellular recognition. Further, sialic acids are contained at high levels in mother's milk and are considered to have a function as an infection protective factor for infants.

In view of the above-described physiological important of sialic acids, a great advancement has been made in the development of techniques for the isolation or extract of sialic acids from milk, including those disclosed in Japanese Patent Publication No. 21234/1965 and Japanese Patent Application Laid-Open No. 184197/1984.

However, the process disclosed in Japanese Patent Publication No. 21234/1965 can isolate only a portion of sialic acids in milk and is therefore not efficient. Further, the process of Japanese Patent Application Laid-Open No. 184197/1984 is adapted to isolate sialic acids at concentrations as high as pure forms. The latter process is therefore accompanied by a problem that its steps are too complex to use it in industrial production.

On the other hand, the following procedures are generally used for the isolation of lactose from whey.

Crude lactose having a lactose content of 85-90% is obtained by conducting a series of steps, which comprise (i) lime treatment and heating of whey, (ii) removal of proteins thus precipitated, (iii) concentration, (iv) cooling and crystallization, (v) centrifugation, and (vi) washing and drying of crystals. Further, purified lactose having a lactose content as high as 95% or even higher is also obtained by proceeding with a series of additional steps, which comprise (vii) dissolution, (viii) discoloration and filtration, (ix) concentration and crystallization, (x) centrifugation, and (xi) drying of crystals.

Although several improvements on lactose production have been made to the above process as a basic process, these processes are all intended to obtain lactose alone and the isolation or recovery of sialic acids is not contemplated of at all. Most of the sialic acids in whey therefore remain in the mother liquor of the crude lactose or in the mother liquor of the purified lactose on the process of centrifugation of above (v) and (x), so that it has been impossible to isolate and recovered lactose and sialic acids together at the same time.

Similarly, skim milk is processed only to recover proteins therefrom. Thus, skim milk is subjected to ultrafiltration or to a heat treatment at a temperature as high as 90° C. or even higher, which is close to the boiling point, whereby the milk proteins are isolated and recovered. Similarly to the case of whey, no attention has therefore been paid for the recovery of sialic acids.

After the recovery of proteins and crude or purified lactose from whey or skim milk, the still remaining mother liquor has heretofore been discarded in general.

SUMMARY OF THE INVENTION

An object of this invention is to provide an advantageous process for isolating and recovering sialic acids simultaneously with lactose from a milk-derived sialic acids-containing liquid such as a permeate obtained by ultrafiltration of whey or skim milk or a deproteinization solution obtained by a heat treatment of whey or skim milk.

In one aspect of this invention, there is thus provided a process for the production of sialic acids-containing lactose, which comprises subjecting a milk-derived sialic acids-containing liquid to desalting, followed by concentration.

More specifically, sialic acids-containing lactose is produced from sialic acid-containing whey or skim milk by subjecting a permeate, which has been obtained by subjecting the whey or skim milk to ultra-filtration, or a deproteinization solution, which has been obtained by subjecting the whey or skim milk to a heat treatment to remove proteins, to (a) electrodialysis, or (b) ion exchange by a cation-exchange resin and a strongly basic anion-exchange resin or (c) a combination of electrodialysis and ion exchange by the cation-exchange resin and the strongly basic anion-exchange resin to desalt the permeate or deproteinization solution and concentrating the thus-desalted permeate or deproteinization solution, and if desired, further seeding and drying the concentrate into powder.

The process of this invention has the advantage that sialic acids can be recovered along with lactose at a low cost by applying simple processing upon production of lactose by desalting of such a permeate or deproteinization solution.

DETAILED DESCRIPTION OF THE INVENTION

The sialic acids-containing whey employed as a starting material in this invention may be obtained as a by-product upon production of lactic acid casein, rennet casein, coprecipitated casein, cheese and/or the like from a milk such as cow's milk, goat's milk or sheep's milk. On the other hand, the skim milk may be obtained by removing milk fat from such a milk.

The whey or skim milk is subjected to deproteinization by ultrafiltration, heating or the like, whereby permeate or deproteinization solution is obtained at the same time that whey proteins or milk proteins are separated and recovered. This permeate or deproteinization solution contains about 1-8 g/100 ml of lactose and about 3-10 mg/100 ml of sialic acids in terms of sialic acid and ash, although their contents vary depending on the kind of whey or skim milk.

The permeate or deproteinization solution obtained in the above manner is preconcentrated to a concentration (solid content) of approximately 5-50% in a concentrator as desired, so that subsequent processing steps may be rendered efficient.

It is desirable to apply a calcium phosphate removal treatment prior to the preconcentration so as to prevent deposition of scale on the concentrator or fouling of a membrane surface upon desalting in an electrodializer.

Next, the permeate or deproteinization solution or a preconcentrate thereof is charged into an electrodialyzer or an ion-exchange resin column to desalt. The dialyzate or column effluent thus obtained is then subjected to final concentration.

In this invention, these processing can preferably be practiced by any one of the following three methods:

Method (1)

The permeate, deproteinization solution or a preconcentrate thereof is subjected only to an electrodialyzer to remove ash, followed by concentration to obtain a desalted lactose concentrate containing sialic acids. In this method, at least 80% of the ash contained in the permeate, deproteinization solution or a preconcentrate thereof is removed by the electrodialyzer. It is also desirable that the subsequent concentration can give a solid content of about 10-50%.

Method (2)

The permeate, deproteinization solution or a preconcentrate thereof is passed through a cation-exchange resin and then through a strongly basic anion-exchange resin, followed by concentration to obtain a desalted lactose concentrate containing sialic acids. In this method, about 90% of the ash contained in the permeate, deproteinization solution or a preconcentrate thereof is removed by the ion-exchange resins. It is also desirable the subsequent concentration can give a solid content of about 10-50%.

Method (3)

This method is a combination of the above method (1) and (2). Namely, the permeate, deproteinization solution or a preconcentrate thereof is subjected first to an electrodialyzer to remove ash. The resulting dialyzate is next passed through the cation-exchange resin and strongly basic anion-exchange resin to remove ash further, followed concentration to obtain a desalted lactose concentrate containing sialic acids. In this method, about 20-70% of the ash contained in the permeate, deproteinization solution or a preconcentrate thereof is removed by the electrodialyzer. Then, 90-98% of the ash is removed by the treatment through the ion-exchange resins. It is also desirable that the subsequent concentration can give a solid content of about 10-50%.

In view of the power consumption, the readiness in cleaning the membrane surface of the electrodialyzer and the resins, and the cost required for the regeneration of the resins, the method (3) using the electrodialyzer and ion-exchange resins in combination is preferred among the above three methods.

It is also preferred to conduct the concentration under reduced pressure.

The ion-exchange resins x-ray may be packed in the form of dual beds by packing two separate columns respectively with the resins or enclosing the resins as discrete beds in a single column. As an alternative, the ion-exchange resins may be enclosed together as a mixed bed in a single resin column.

On the ion-exchange resins, the cation-exchange resin may be either a strongly acidic cation-exchange resin or a weakly acidic cation-exchange resin. Examples of such resins include Amberlite IR-120, Amberlite IRC-50, Duolite D-20HC, Duolite C-464, Duolite C-225, Diaion SK1B, Diaion PK208, Dowex ECR-S and Dowex CCR-2, all trade names and etc.

On the other hand, the use of a weakly basic anion-exchange resin in lieu of the strongly basic anion-exchange resin results in adsorption of sialic acids, which are contained in the permeate or deproteinization solution, along with ash on the resin so that the sialic acids cannot be recovered. It is hence impossible to use a weakly basic anion-exchange resin. It is only a strongly basic anion-exchange resin that can be used.

Examples of the strongly basic anion-exchange resin include Duolite A-116, Amberlite IRA-416, Amberlite IRA-410, Diaion PA 418, Dowex 11, all trade names and etc.

When the ion-exchange resins are used in the above method (2) or (3), it is most suitable that permeate, deproteinization solution or preconcentrate thereof is passed through theme under the following flow conditions: superficial column velocity (SV): 2-7, concentration (solid content): 5-40%, and temperature: 5°-50° C. However, the superficial column velocity may be chosen from any range as long as a desired desalting rate (80-98%) can be achieved. Similarly, it is not absolutely necessary to limit the concentration and temperature to the above ranges as long as crystallization of lactose is avoided.

Table 1 shows the recovery rates of sialic acids and desalting rates when a permeate of whey was separately treated by various ion-exchange resins in accordance with the method (3) to produce desalted lactose containing the sialic acids.

TABLE 1

| Anion-exchange resin | Cation-exchange resin | Recovery rate of sialic acids (%) | Desalting rate (%) |
| --- | --- | --- | --- |
| Weakly basic | | | |
| Duolite A-368 | Amberlite IRC-50 | 0-30 | 90-99 |
| Amberlite IRA-93 | Amberlite IR-120B | | |
| Dowex MWA-1 | Duolite C-2D | | |
| Strongly basic | Dowex CCR-2 | | |
| Duolite A-116 | Duolite C-225 | 70-100 | 90-99 |
| Amberlite IRA-410 | | | |

TABLE 1-continued

| Anion-exchange resin | Cation-exchange resin | Recovery rate of sialic acids (%) | Desalting rate (%) |
| --- | --- | --- | --- |
| Amberlite IRA-416 | | | |
| Diaion PA 418 | | | |
| Dowex 11 | | | |

In Table 1, the recovery rates of sialic acids and desalting rates were calculated on the basis of the contents of the sialic acids and ash contained in the permeate before the respective processing.

As is readily envisaged from Table 1, the use of the weakly basic anion-exchange resins gave a desalting rate in the range of 90-99%. As far as the desalting rate is concerned, they were able to achieve the goal. However, the recovery rates of the sialic acids ranged from 0% to 30% and were hence extremely low. They are accordingly unsuitable for the object of this invention. This is because sialic acids were adsorbed together with ash on the resins as described above so they cannot be recovered. When the strongly basic anion-exchange resins were used, the object of the present invention was fulfilled in both desalting rate and recovery rate of sialic acids.

It is therefore essential to use a strongly basic anion-exchange resin and a cation-exchange resin in combination when ion-exchange resins are used in the process of this invention.

The desalted sialic acids-containing lactose obtained in the above-described manner is in the form of a concentrate. Addition of the concentrate to other food stocks, for example, formulated milk for producing powdered milk or the like or to liquid drinks makes it possible to provide foods imparted with physiologically active functions derived from sialic acids, such as infection protective ability, cytotoxicity neutralizing ability and learning ability.

In addition, the desalted lactose concentrate obtained in the above-described manner and containing sialic acids may be subjected to seeding and then to drum drying or spray drying, thereby converting it into desalted lactose powder containing sialic acids in a powder form. In this case, α-lactose or the like may be added before the seeding. The powdered lactose thus obtained can improve the handling and storability.

The term "lactose" as used herein means not only lactose itself but also lactose concentrates and dry lactose powder.

The present invention will hereinafter be described specifically by the following examples.

EXAMPLE 1

By an ultrafiltration apparatus, whey proteins (hereinafter abbreviated as "WPC") were separated out from 100 l of whey obtained as a byproduct upon production of rennet casein. Ninety liters of the resultant permeate were adjusted to pH 6.4 with caustic soda and then maintained at 70° C. for 5 minutes. Calcium phosphate was removed by a clarifier, followed by the pH adjustment to 5.2 with hydrochloric acid.

After preconcentration of the permeate to a solid content of 25% in a evaporator, it was fed to an electrodialyzer to remove 65% of the ash. Furthermore, the resultant dialyzate was passed through a cation-exchange resin (Duolite C-20) and a strongly basic anion-exchange resin (Amberlite IRA-410), both at SV=2.5 and 20° C. to remove 95% of the ash.

The thus-desalted permeate was then subjected to final concentration in a evaporator until the solid content increased to 50%. The concentrate was added with α-lactose and after seeding, it was dried in a spray drier to obtain 4 kg of desalted lactose powder containing sialic acids.

The thus-obtained lactose powder had the following composition, per 100 g: lactose: 92.7 g, water: 5.0 g, ash: 0.3 g, sialic acids in terms of sialic acid: 70 mg.

EXAMPLE 2

By an ultrafiltration apparatus, WPC was separated out from 100 l of whey which had been obtained as a byproduct upon production of Gouda cheese. After preconcentration of 90 l of the resultant permeate to a solid content of 20%, it was passed through an electrodialyzer to remove 60% of the ash. The resultant dialyzate was passed through a cation-exchange resin (Duolite C-225) and a strongly basic anion-exchange resin (Amberlite IRA-416), both at SV=5.0 and 30° C. to remove 95% of the ash.

The thus-desalted permeate was then subjected to final concentration in a evaporator until the solid content increased to 50%, thereby obtaining 9 kg of a desalted lactose concentrate containing sialic acids.

The thus-obtained lactose concentrate had the following composition, per 100 g: lactose: 46.1 g, ash: 0.3 g, sialic acids in terms of sialic acid: 35 mg.

Next, 20.9 kg of the lactose concentrate obtained as described above were added with a solution which contained 41.7 kg of whey powder and 1 kg of vitamin and mineral components in 500 kg of water. Further, 239 kg of skim milk and 23.9 kg of vegetable oil were added, followed by homogenization. The resultant solution was sterilized, and concentrated and dried by methods known per se in the art to obtain 100 kg of powdered milk.

EXAMPLE 3

By an ultrafiltration apparatus, WPC was separated out from 100 l of whey which had been obtained as a byproduct upon production of lactic acid casein. The resultant permeate (90 l) was passed through a cation-exchange resin (Amberlite IR-120) and a strongly basic anion-exchange resin (Duolite A 116), both at SV=6.0 and 40° C. to remove 95% of the ash.

The thus-desalted permeate was then subjected to concentration in a evaporator until the solid content increased to 50%, thereby obtaining 9 kg of a desalted lactose concentrate containing sialic acids.

The thus-obtained lactose concentrate had the following composition, per 100 g: lactose: 46.3 g, ash: 0.4 g, sialic acids in terms of sialic acid: 40 mg.

EXAMPLE 4

Whey (100 l) which had been obtained as a byproduct upon production of lactic acid casein was adjusted to pH 5.5 with hydrochloric acid. After addition of 0.13% of calcium chloride, the resultant mixture was heated to 96° C. After holding the mixture at the same temperature for 7 minutes, WPC was removed by a centrifugator.

After preconcentration of 90 l of the resultant solution to a solid content of 25% in a evaporator, the deproteinization solution was passed through an electrodialyzer to remove 70% of the ash. The resultant dialyzate was then passed through a cation-exchange resin (Dowex CCR-2) and a strongly basic anion-exchange resin (Diaion PA 418), both at SV=2.5 and 20° C. to remove 95% of the ash.

The thus-desalted column effluent was next subjected to final concentration in a evaporator until the solid content increased to 50%, thereby obtaining 9 kg of a desalted lactose concentrate containing sialic acids.

The thus-obtained lactose concentrate had the following composition, per 100 g: lactose: 46.2 g, ash: 0.15 g, sialic acids in terms of sialic acid: 40 mg.

EXAMPLE 5

By an ultrafiltration apparatus, milk proteins were separated out from 100 l of skim milk. The resultant permeate (90 l) was passed through a cation-exchange resin (Amberlite IR-120B) and a strongly basic anion-exchange resin (Duolite A-116), both at SV=4.0 and 25° C. to remove 95% of the ash.

The thus-desalted permeate was then subjected to concentration in a evaporator until the solid content increased to 45%, thereby obtaining 8.5 kg of a desalted lactose concentrate containing sialic acids.

The thus-obtained lactose concentrate had the following composition, per 100 g: lactose: 47.0 g, ash: 0.5 g, sialic acids in terms of sialic acid: 50 mg.

EXAMPLE 6

Skim milk (100 l) was adjusted to pH 4.7 with hydrochloric acid and then heated to 93° C. After holding it at that temperature for 7 minutes, milk proteins were removed by a decanter.

After preconcentration of 80 l of the deproteinization solution to a solid content of 15% in a evaporator, the deproteinization solution through an electrodialyzer to remove 50% of the ash. The resultant dialyzate was then passed through a cation-exchange resin (Diaion SK1B) and a strongly basic anion-exchange resin (Dowex 11), both at SV=3 and 30° C. to remove 95% of the ash.

The thus-desalted column effluent was next subjected to final concentration in a evaporator until the solid content increased to 50%. The concentrate was added with α-lactose and after seeding, was dried in a spray drier to obtain 4.5 kg of desalted lactose powder containing sialic acids.

The thus-obtained lactose powder had the following composition, per 100 g: lactose: 90.0 g, water: 5.0 g, ash: 0.5 g, sialic acids in terms of sialic acid: 90 mg.

We claim:

1. A process for the production of sialic acids-containing lactose, which comprises the steps of subjecting a deproteinized solution having a 5-40% solids content obtained by subjecting sialic acids-containing whey or skim milk to ultrafiltration or to a heat treatment to remove proteins, to ion exchange by a cation-exchange resin and a strongly basic anion-exchange resin at a SV of 2-7 and a temperature of 5°-50° C., alone or in combination with electrodialysis, to desalt the solution to an extent of at least 80; and then concentrating the thus-desalted solution to a 10-50% solids content; and recovering the thus-produced sialic acids-containing lactose product.

2. The process of claim 1, wherein the deproteinized solution is first subjected to desalting by electrodialysis to effect removal of at least 80% of ash in the permeate or deproteinization solution followed by ion exchange with the strongly basic anion-exchange resin.

3. The process of claim 1, comprising the further steps of seeding and drying the resultant concentrate.

4. The process of claim 1, wherein the desalting is effected by first removing 20-70% of ash by electrodialysis and then removing 90-98% of the ash with the ion-exchange resins.

5. The process of claim 3, wherein the desalting is effected by passing the permeate or deproteinization solution through the ion exchange resins under conditions of a concentration (solid content) of 5-40%, a flow rate (SV) of 2-7 and a temperature of 5°-50° C.

6. The process of claim 4, wherein the desalting is effected by passing the permeate or deproteinization solution through the ion exchange resins under conditions of a concentration (solid content) of 5-40%, a flow rate (SV) of 2-7 and a temperature of 5°-50° C.

7. The process of claim 1, comprising the further step of seeding and drying the resultant concentrate into a powder.

* * * * *